United States Patent
Petrolli et al.

(10) Patent No.: US 7,169,736 B2
(45) Date of Patent: Jan. 30, 2007

(54) CATALYST FOR HYDROGENATION OF UNSATURATED HYDROCARBONS

(75) Inventors: Mauro Petrolli, München (DE); Ingrid Geyer, Kaufbeuren (DE); Francesco Casagrande, Sesia (IT)

(73) Assignee: Süd-Chemie AG, München (DE)

( * ) Notice: Subject to any disclaimer, the term of this patent is extended or adjusted under 35 U.S.C. 154(b) by 154 days.

(21) Appl. No.: 10/203,331

(22) PCT Filed: Feb. 8, 2001

(86) PCT No.: PCT/EP01/01365

§ 371 (c)(1),
(2), (4) Date: Nov. 11, 2003

(87) PCT Pub. No.: WO01/58590

PCT Pub. Date: Aug. 16, 2001

(65) Prior Publication Data

US 2004/0133052 A1 Jul. 8, 2004

(30) Foreign Application Priority Data

Feb. 10, 2000 (DE) ............................... 100 05 775
Sep. 28, 2000 (DE) ............................... 100 48 219

(51) Int. Cl.
*B01J 23/00* (2006.01)
*B01J 23/40* (2006.01)
*B01J 23/42* (2006.01)
*B01J 23/58* (2006.01)
*B01J 23/44* (2006.01)

(52) U.S. Cl. .................. 502/327; 502/328; 502/330; 502/332; 502/333; 502/339; 502/348; 502/355; 502/415; 502/439; 502/527.17

(58) Field of Classification Search ............... 502/327, 502/328, 330, 332, 333, 339, 348, 355, 415, 502/439, 527.17
See application file for complete search history.

(56) References Cited

U.S. PATENT DOCUMENTS 4,199,436 A * 4/1980 County ...................... 208/124

(Continued)

FOREIGN PATENT DOCUMENTS

EP 0464633 1/1992

(Continued)

OTHER PUBLICATIONS

C.F. Datasheets "Girdler Catalysts G-58C, G-58D, G-58H, G-58I, G-83 for Selective Hydrogenation" From Jan. 1998.

*Primary Examiner*—Cam N. Nguyen
(74) *Attorney, Agent, or Firm*—Scott R. Cox

(57) ABSTRACT

A catalyst is described for hydrogenation of unsaturated hydrocarbons, containing catalytically active amounts of Pd and optionally Ag in a support. The catalyst is characterized by the fact that the support represents a shaped body with a trilobal cross section, the lobes being provided with continuous openings. The catalysts can be produced according to a method, in which the support is impregnated with a solution of salts of Pd and optionally Ag. These salts are reduced by means of a reducing agent, whereupon the support so impregnated is washed, dried and calcined and, if reduction is not complete, the still present oxides of Pd and Ag are reduced to the corresponding metals in a hydrogen-containing atmosphere.

22 Claims, 1 Drawing Sheet

U.S. PATENT DOCUMENTS

| | | | |
|---|---|---|---|
| 5,149,680 A * | 9/1992 | Kitson et al. | 502/185 |
| 5,330,958 A | 7/1994 | Viola et al. | |
| 5,475,173 A | 12/1995 | Cheung et al. | |
| 5,488,024 A | 1/1996 | Cheung et al. | |
| 5,489,565 A * | 2/1996 | Cheung et al. | 502/325 |
| 5,510,550 A | 4/1996 | Cheung et al. | |
| 5,583,274 A | 12/1996 | Cheung et al. | |
| 5,585,318 A | 12/1996 | Johnson et al. | |
| 5,587,348 A | 12/1996 | Brown et al. | |
| 5,648,576 A | 7/1997 | Nguyen Than et al. | |
| 5,750,790 A * | 5/1998 | King | 564/469 |
| 5,861,353 A | 1/1999 | Viola et al. | |
| 5,866,735 A * | 2/1999 | Cheung et al. | 585/273 |
| 5,939,351 A | 8/1999 | Rubini et al. | |
| 5,965,481 A * | 10/1999 | Durand et al. | 502/304 |
| 5,977,012 A * | 11/1999 | Kharas et al. | 502/326 |
| 6,054,409 A | 4/2000 | Nguyen Thanh et al. | |
| 6,127,588 A * | 10/2000 | Kimble et al. | 585/260 |
| 6,147,027 A * | 11/2000 | Miyake et al. | 502/325 |
| 6,350,717 B1 * | 2/2002 | Frenzel et al. | 502/330 |
| 6,437,206 B1 * | 8/2002 | Meyer et al. | 585/260 |
| 6,635,600 B1 * | 10/2003 | Kimble et al. | 502/330 |

FOREIGN PATENT DOCUMENTS

| | | | |
|---|---|---|---|
| EP | 0464633 A1 * | 1/1992 | |
| EP | 0689872 A1 * | 1/1996 | |
| EP | 0722776 | 7/1996 | |

* cited by examiner

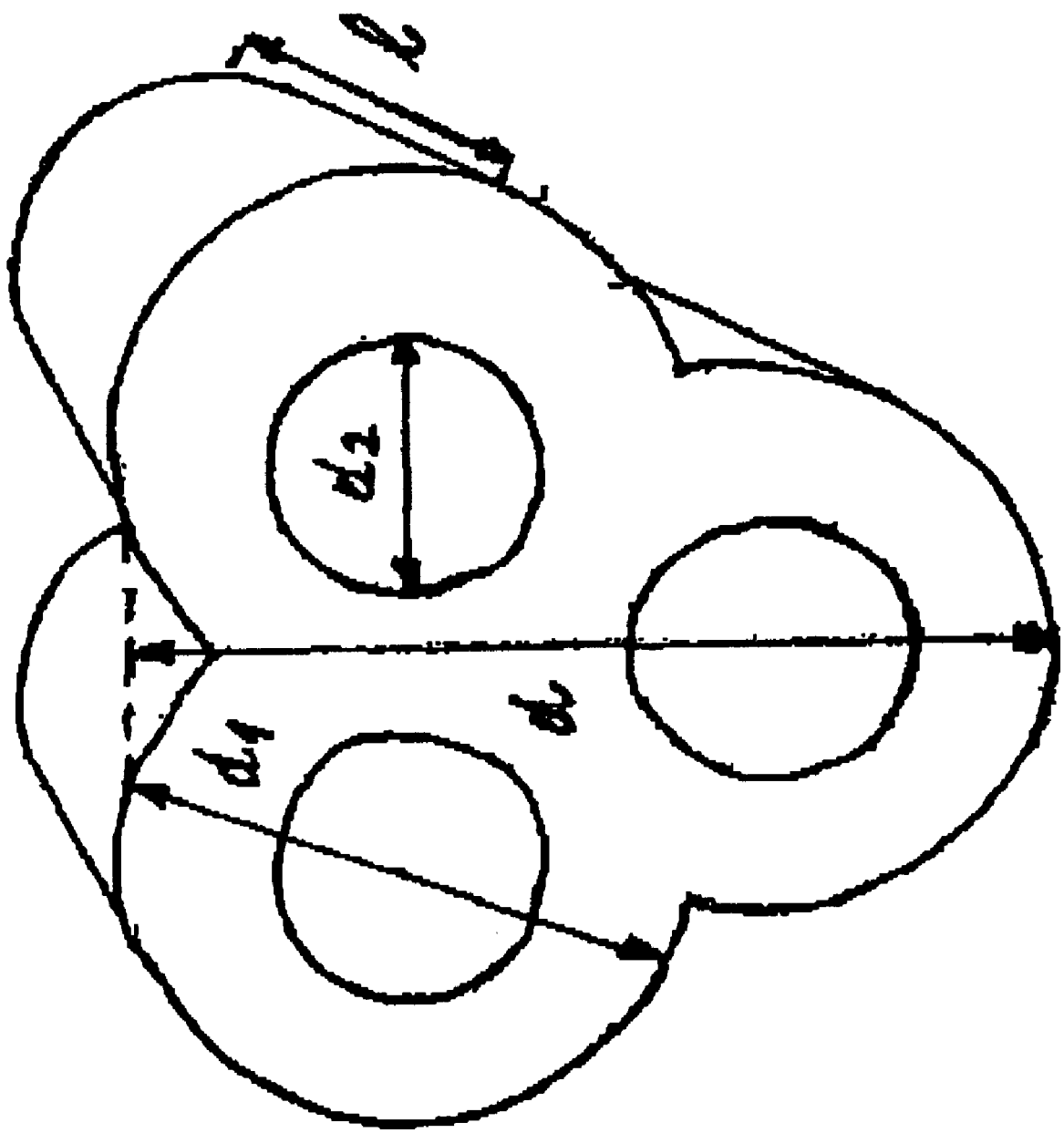

CATALYST FOR HYDROGENATION OF UNSATURATED HYDROCARBONS

BACKGROUND OF THE INVENTION

The invention concerns a catalyst for hydrogenation of unsaturated hydrocarbons.

A method for catalytic hydrogenation of acetylenic compounds with 2 or 3 carbon atoms to the corresponding olefin compounds is known from EP-A-0 686 615, in which a supported catalyst in the form of spheres or extrudate is used, containing palladium and silver. At least 80% of the palladium and at least 60% of the silver are located close to the surface of the catalyst. The catalyst preferably contains aluminum oxide as a support and 0.01 to 0.5 wt. % palladium and 0.001 to 0.002 wt. % silver. Because of the form of the support, the activity and selectivity, in relation to the weight, are relatively low. Only a relatively low space velocity can be used with this catalyst and the pressure drop is relatively high.

A catalyst, containing Pd and Ag for selective hydrogenation of acetylene, is known from EP-A-0 689 872. The catalyst is produced by treating a support material (preferably aluminum oxide) in the form of spheres or cylindrical pellets, with an alkaline solution of reducing agent for Pd and Ag.

A supported catalyst for diolefin hydrogenation, containing palladium, silver and an alkali fluoride is known from EP-A-0 693 315. Spherical pellets or cylindrical extrudates are preferably used as support.

A catalyst for hydrogenation of $C_2$ to $C_{10}$ alkynes, preferably acetylene, to the corresponding alkenes in the presence of sulfur compounds is known from EP-A-0 738 540, which contains palladium, silver, at least one chemically bonded alkali metal (preferably K), chemically bonded fluorine and an inorganic support (preferably aluminum oxide) in the form of pellets.

EP-A-0 732 146 describes catalysts, whose supports represent molded bodies with a trilobal cross section and through openings. The catalysts contain iron oxide-molybdenum. oxide compounds as catalytically active components. The catalysts are used specifically for oxidation of methanol to formaldehyde, although some other applications not demonstrated by examples are stated (for example, hydrogenation of acetylene and olefins).

EP-A-464 633 describes catalysts, whose support represents molded bodies with a trilobal cross section and continuous openings (cf. FIG. 5). The catalysts contain a mixture of elements of groups VIII and 1B of the Periodic Table, especially palladium and gold, as the catalytically active components. They are used for conversion of olefins with organic carboxylic acids and oxygen to unsaturated esters, especially for production of vinyl acetate from ethylene and acetic acid.

EP-B-591 572 describes a catalytic material in the form of particles with a trilobal cross section and at least three continuous pore openings, as well as a specific ratio between height of the particles and spacing between the axes of the holes. This material is used for oxidative dehydrogenation of methanol to produce formaldehyde.

Catalysts for selective hydrogenation of diolefins and alkynes to mono-olefins and alkenes are also marketed by the applicant under the names G-58 and G-83, which contain palladium and silver on a spherical support or on a support in the form of solid pellets or extrudates (cf. data sheets "Girdler Catalysts G-58 C, G-58 D, G-58 H, G-58 I and G-83 for Selective Hydrogenation", from January 1998).

Catalysts on such supports generally have the drawback that their activities and selectivities are relatively low and hydrogenation reactions can only be run at relatively low space velocities. These catalysts also have relatively high flow resistance.

The task underlying the present invention is to eliminate these shortcomings. It was surprisingly found that these shortcomings could be eliminated by using a catalyst whose support has a specific shape.

The object of the invention is therefore a catalyst for hydrogenation of unsaturated hydrocarbons, containing catalytically effective amounts of Pd and optionally Ag on a support. The catalyst is characterized by the fact that the support represents a shaped body with a trilobal cross section, in which the lobes are provided with through openings.

BRIEF DESCRIPTION OF THE DRAWINGS

FIG. 1 is a perspective view of the catalyst of the invention.

DETAILED DESCRIPTION OF INVENTION

The catalyst according to the invention ordinarily has a geometric surface (GS) of about 0.2 to 3 $cm^2$, preferably about 0.7 to 1.9 $cm^2$, especially about 0.9 to 1.5 $cm^2$ per shaped body.

The ratio ($R_1$) between length (l) and diameter (d) of the trilobal shaped body (See FIG. 1) is preferably in the range of the following:

$$R_1 = l/d = 2-4$$

The ratio ($R_2$) between geometric surface (GS) of the shaped body and volume of the solid fraction of the shaped body ($V_f$) preferably is:

$$R_2 = GS/V_f = 0.5-20 (mm^{-1}), \text{ in particular } 1.4-(mm^{-1}).$$

Pd is preferably present in amounts of about 0.01 to 1.5 wt. % and Ag in amounts of about 0.1 to 0.5 wt. %, based on the weight of the support material, and the weight ratio between Pd and Ag is about 0.1 to 5.0.

The penetration depth of the catalytically active component (Pd and optionally Ag) into the support as shaped bodies after reduction is preferably wherein at least about 80% of the active components are within 60 to 300 μm of the surface.

The crystallite size of the Pd crystallites after reduction is about 2 to 15 nm, based on 80% of the Pd crystallites, and the ratio ($R_3$) between the BET surface and the size of the Pd crystallites ($d_{Pd}$) is preferably as follows:

$$R_3 = BET-S/dp_d = 0.1-10$$

The size of the Pd crystallites is determined according to the CO adsorption method according to the literature reference Journal of Catalysis 25, 148–160 (1972).

Aluminum oxide, especially θ-aluminum oxide, is preferably used as the support. This component is generally not present in pure form, but can also be present in other aluminum oxide forms, like α-aluminum oxide. Titanium dioxide, zirconium dioxide, silicon dioxides zinc oxide, silicon carbide or talc, however, can also be used.

The BET surface area of the support is about 1 to 300 $m^2/g$, preferably about 10 to 300 $m^2/g$, especially about 30 to 80 $m^2/g$. The BET surface area is determined according to the one-point method by nitrogen adsorption according to DIN 66132.

About 40% of the BET surface area is situated in pores with a diameter of about 1570 to 80 nm and about 60% is situated in pores with a diameter of about 80 to 14 nm. Pore volume and distribution of specific surface areas to specific pore sizes is determined according to DIN 66133 (Hg porosimetry).

The trilobal shaped body used as support according to the invention are explained in the accompanying drawing FIG. 1 wherein (d) denotes the diameter, (l) the length of the trilobal shaped body, d1 denotes the diameter of one lobe and d2 the diameter of the opening in a lobe.

The diameter (d) of the trilobal shaped body is preferably about 3 to 10 mm, the length (l) is about 3 to 15 mm, and the diameter of an opening in a lobe (d2) is about 0.5 to 5 mm.

The catalysts according to the invention preferably also contain limited amounts of alkali and/or alkaline earth metals, especially about 0.01 to 0.1 wt. % (calculated as oxides).

Relative to known catalysts, the catalysts according to the invention are characterized by high activity and selectivity. Higher space velocities of about 12000 to 15000 can also be used (volume parts of reactants in the gaseous state per volume part of catalyst and hour=GSHV), compared with a space velocity of only about 3000 to 8000 if spheres, solid pellets or extrudates are used. The catalysts according to the invention also exhibit lower pressure drops (up to 60% relative to spherical or pellet-like supports (115% and 100%)) .

An object of the invention is also a method for production of the catalysts just defined, in which the support is impregnated with a solution of salts of Pd and optionally Ag ($PdCl_2$, $H_2PdCl_4$ and $AgNO_3$) and the salts reduced with a reducing agent (e.g., sodium formate, $NaBH_4$, hydrazine, formaldehyde, ascorbic acid, citric acid, Na acetate, oxalic acid, etc.), and preferably in an alkaline medium at temperatures between about 20 and 100° C., preferably in the range from 40 to 60° C.

The reduction is preferably run in an aqueous-alkaline solution. In this variant of the method, the Pd and optionally Ag oxide is fixed on the surface of the support and reduced there to the corresponding metals. In this manner, the penetration depth of the metal can be controlled to about 60 to 300 μm.

As an alternative, reduction can be run with a reducing agent in a nonaqueous solvent, if the reducing agent is decomposed by water. This is especially true for $NaBH_4$ and other hydrides or double-hydrides, like $LiAlH_4$, $LiBH_4$, $CaH_2$ or $LaH_3$.

The impregnated support is generally washed, dried and calcined. If reduction is not complete and Pd and Ag are still present partially in the form of their oxides, these are reduced to the corresponding metals by heating in a hydrogen-containing atmosphere (forming). Forming, however, can also occur in the reactor, in which case only hydrogen is initially introduced before introduction of the compounds being hydrogenated.

The shaped bodies are generally produced by mixing the support material with water, a binder (like carboxymethylcellulose) and/or a lubricant (for example, an alkaline earth or aluminum stearate).

Production of the shaped bodies occurs in a pellet press with a rotary plate, on whose periphery several openings with trilobal cross section are arranged. The mixture is filled into these openings (matrices) and held from the bottom by a ram, through which three pins that lie at the sites of the openings to be produced are pushed upward during rotation of the rotary plate, On further rotation of the rotary plate, a ram with a trilobal cross section engages from the top, which is provided with openings, into which the pins in the lower ram penetrate during pressing down of the upper ram. The pressed shaped bodies, during further rotation of the rotary plate, are forced out of the matrices after retraction of the lower ram and further advance of the upper ram. The "green" shaped bodies are dried and calcined. Pores with the desired site are formed in the shaped bodies.

The shaped bodies are then impregnated with a solution of salts of palladium and optionally silver, in which an alkaline solution is added after impregnation, in order to precipitate palladium and silver in the form of the corresponding oxides.

The solution of a reducing agent is then added, which reduces the oxides to the corresponding metal. However, it is also possible to use an alkaline reducing agent solution.

After precipitation of the oxides or metals of the catalytically active component(s), the shaped bodies are washed, in order to eliminate soluble salts (for example, NaCl and $NaNO_3$). The shaped bodies are then dried and calcined, whereupon any still present oxides of the catalytically active component(s) are reduced to the corresponding metals. Reduction generally occurs in a hydrogen atmosphere at temperatures from about 20 to 450° C. Reduction can also occur in a reactor, in which case hydrogen or a hydrogen-containing gas is introduced before introduction of the compounds to be hydrogenated.

Finally, an object of the invention is use of the aforementioned catalysts for hydrogenation of unsaturated hydrocarbons, especially for selective hydrogenation of diolefins to mono-olefins or acetylenes to olefins.

The invention is explained by the following examples;

EXAMPLE 1

1000 parts by weight boehmite is mixed with 10 parts by weight water and 40 parts by weight magnesium stearate to a homogeneous, pressable mass. This mass is introduced into the openings of a rotary plate of the pellet press just described, whose cross sections correspond to the depicted shape (d=6 mm, d1=4 mm, d2=1.5 mm, l =6 mm). The shaped bodies are then pressed, as described above, and ejected from the pellet press. The obtained shaped bodies are dried for two hours at 120° C. and calcined for 4.5 hours at 1075° C., in which the boehmite is largely converted to θ-aluminum oxide (in addition to some α-aluminum oxide) The geometric surface is 1.3 $cm^2$ per shaped body. The BET surface area is then determined according to DIN 66132 at 30 $m^2$/g. The pore volume is then determined according to DIN 66133 at 0.35 mL/g, as well as the pore distribution. 40% of the BET surface area is contained in pores with a diameter from 1750 to 80 nm, 60% of the BET surface area is contained in pores with a diameter from 80 to 14 nm.

An $H_2PdCl_4$ solution (0.345 parts by weight palladium) in 1150 parts by weight distilled water is rapidly added to 1000 parts by weight of the shaped bodies and slowly mixed for 5 minutes. The mixture is allowed to stand for about 60 minutes and the decolored solution then drained off.

The moist product is immediately mixed with roughly 40° C. warm 5% sodium formate solution and allowed to stand for 2.5 hours. The formate solution is then drained off and the product is washed chloride-free with distilled water. The product is then calcined at 540° C. for two hours.

1000 parts by weight of the calcined product is added to a solution of 3.13 parts by weight AgNO$_3$ in 1150 parts by weight distilled water and mixed slowly for 5 minutes. The mixture is allowed to stand for two hours and the solution then discharged. The product is calcined for 2.5 hours at 540° C.

The molded articles so obtained are filled into a tubular reactor that is initially flushed with nitrogen. Hydrogen, at a temperature of 400° C., is then passed through for 8 hours, so that the palladium and silver on the shaped bodies are fully reduced. A mixture of 1.1 vol. % acetylene and 1.5 vol. % hydrogen in ethylene at a temperature of 50° C., a pressure of 2.5 MPa and a space velocity of 14000 liters of mixture per kg of catalyst per hour is then passed through the reactor. The acetylene is 54% converted to ethylene with a selectivity of 93%.

COMPARATIVE EXAMPLE 1

A spherical catalyst support produced from θ-Al$_2$O$_3$ with a diameter of 2 to 4 mm, a geometric surface of 0.3 cm$^2$, a BET surface area of 30 mg$^2$/g, a pore volume of 0.39 mL/g and a pore volume distribution of 40% between 1750 and 80 nm and 60% between 80 and 14 nm is impregnated with the H$_2$PdCl$_4$/AgNo$_8$ solution of example 1 and reduced, dried, calcined and formed in the same manner as described in example 1 The catalyst is used for selective hydrogenation of acetylene to ethylene as in example 1, in which the same process conditions are employed. The acetylene is 50% converted to ethylene with a selectivity of 65% at a space velocity of 8000 (liter of reactants per liter of catalyst per hour).

COMPARATIVE EXAMPLE 2

The procedure of comparative example 1 was repeated with the deviation that a catalyst in the form of 4×4 mm pellets was used, all other conditions remaining unchanged. The acetylene was 48% converted to ethylene with a selectivity of 76%.

The catalyst according to example 1 and according to comparative examples 1 and 2 were measured in a separate pressure loss tube (with nitrogen as measurement gas ), the following pressure loss relation being determined: example 1: 60%; comparative example 1: 115%; comparative example 2: 100%.

EXAMPLE 2

The procedure of example 1 was repeated with the deviation 5 that the support was calcined for 4.5 hours at 1020° C. and the support so treated was coated with 0.3 wt. % palladium. The catalyst had a BET surface area of 70±5 cm$^2$/g, a pore volume of 0.4 mL/g with 4.71% of the surface in pores with a diameter of 1750 to 80 nm and 76% in pores with a diameter of 80 to 14 nm. The rest of the surface pertained to pores with a diameter of <14 nm.

The catalyst shaped bodies were formed according to example 1 in a tubular reactor for 8 hours at 400° C. and exposed to a mixture of hydrogen and a diene-containing pyrolysis gasoline (2 mol H$_2$, 1 mol diene) first at 30° C. and then at 60° C., a pressure of 3.0 MPa and a space velocity of 8 volume parts liquid pyrolysis gasoline per volume part catalyst and hour (LHSV). The composition of the pyrolysis gasoline before selective hydrogenation is shown in Table 1.

TABLE I

|  | MOL % |
| --- | --- |
| benzene | 38.6 |
| toluene | 22.6 |
| o-xylene | 1.7 |
| p-xylene | 4.1 |
| m-xylene | 2.0 |
| ethylbenzene | 2.0 |
| styrene | 6.0 |
| cyclohexane | 0.7 |
| methylcylcohexane | 1.5 |
| hexadiene | 1.2 |
| cyclohexadiene | 0.3 |
| hexane | 10.2 |
| heptane | 1.4 |
| heptene | 8.9 |

The styrene and diene conversions, as well as the diene selectivity after selective dehydrogenation are shown in Table II.

TABLE II

| Hours | Temperature | Styrene conversion | Diene conversion | Diene selectivity |
| --- | --- | --- | --- | --- |
| 24 | 30 | 98.6 | 99.2 | 81.3 |
| 48 | 30 | 98.6 | 98.9 | 81.0 |
| 12 | 30 | 98.9 | 99.5 | 79.8 |
| 96 | 60 | 100 | 100 | 70.7 |
| 144 | 60 | 100 | 99.8 | 69.8 |
| 170 | 60 | 100 | 99.8 | 69.2 |

COMPARATIVE EXAMPLE 2

The procedure of example 2 was repeated, with the deviation that catalysts in the form of spheres with a diameter of 2 to 4 mm with a palladium coating of 0.3%, a geometric surface of 0.3 cm$^2$, a BET surface area of 70±5 cm$^2$/g, a pore volume of 0.5 mL/g and a pore distribution as the catalyst of example 2 were exposed to pyrolysis gasoline with the composition stated in Table I at an initial temperature of 30° C. and later 60° C., a pressure of 3.0 MPa and an LHSV of 4. The styrene and diene conversions, as well as the diene selectivity after selective hydrogenation, are shown in Table III.

TABLE III

| Hours | Temperature | Styrene conversion | Diene conversion | Diene selectivity |
| --- | --- | --- | --- | --- |
| 24 | 30 | 83.7 | 81.7 | 60.9 |
| 48 | 30 | 84.5 | 61.7 | 59.6 |
| 72 | 30 | 81.7 | 81.9 | 57.9 |
| 96 | 60 | 95.7 | 91.7 | 50.3 |
| 144 | 60 | 95.6 | 91.5 | 45.5 |
| 170 | 60 | 95.7 | 91.6 | 40.8 |

EXAMPLE 3

According to the procedure of example 1 of EP-0 314 024-A1, a commercial titanium dioxide (P-25 Degussa) is homogenized in an intensive mixer with addition of about 55 wt. % water and 14 wt. % isopropyl titanate for 45 minutes. After several hours of drying at 110° C., the TiO$_2$ mass is subjected to size reduction, mixed with aluminum stearate as pelletizing agent and pressed into shaped bodies with a trilobal cross section according to example 1 (dimensions as in example 1).

The $TiO_2$ shaped bodies are calcined for 3 hours at 550° C. in an oxidizing atmosphere.

The geometric surface was 1.3 cm² per shaped body, the BET surface area 36 m²/g, the pore volume 0.39 mL/g, 3.7% of the BET surface area pertained to pores with a diameter from 1750 to 80 nm, and 95.8% pores with a diameter of 80 to 14 nm.

The $TiO_2$ support was spray-impregnated with an 8% aqueous sodium formate solution (30 mL formate solution per 100 g support). The support so pretreated was then spray-impregnated with the same volume of a 2.5% aqueous $PdCl_2$ solution. The support shaped bodies were immersed in a formate solution, filtered by suction and washed chloride-free for complete reduction of the noble metal. After drying at 100° C., they were calcined for 6 hours to a final temperature of 400° C. Promotion with silver was then carried out. For this purpose, the palladium-containing $TiO_2$ shaped bodies were impregnated at room temperature with silver nitration solution, dried at 110° C. and calcined for another 6 hours to a temperature of 360° C. The palladium content was 0.21 wt. %, the silver content 0.12 wt. %.

The catalyst was used at a pressure of 0.15 MPa, a temperature of 120° C. and a LHSV of 15 h$^{-1}$, with a molar ratio $H_2$/diene of 2:1 for selective hydrogenation of a liquid diene-containing mixture with the composition 85.7 mol % paraffin
11.1 mol % mono-olefin
0.85 mol % dienes
2.40 mol % aromatics.

Diene conversion was 80% at a selectivity of 85%.

COMPARATIVE EXAMPLE 3

The procedure of example 3 is repeated, with the deviation that solid pellets, with dimensions of 4.5×4.5, were used instead of the trilobal shaped bodies, and they were coated in the same manner as in example 3 with the catalytically active metals. The support had a BET surface area of 33 m²/g and a pore volume of 0.2 mL/g, 51% of the BET surface area pertaining to pores with a diameter from 1750 to 80 nm, 87.3% of the pores with a diameter from 80 to 14 nm. The catalysts contained 0.213 wt. % Pd and 0.27 wt. % Ag.

The catalyst was used for selective hydrogenation of the diene-containing mixture used in example 3 (LHSV=10 H$^{-1}$, T=120° C., pressure=0.15 MPa, molar ratio $H_2$:diene=4:1).

The diene conversion was 70% at a selectivity of 60%.

The invention claimed is:

1. A catalyst for hydrogenation of unsaturated hydrocarbons comprising catalytically active amounts of palladium on a support, wherein the support is a shaped body with a trilobal cross-section, wherein lobes of the trilobal shaped body are provided with openings passing therethrough and wherein a ratio between a length and a diameter of the trilobal shaped bodies is from about 2:1 to about 4:1.

2. The catalyst of claim 1 further comprising catalytically active amounts of silver.

3. The catalyst of claim 2 wherein the palladium comprises from about 0.01 to 1 weight percent and the silver comprises from 0.1 to 0.5 weight percent of the catalyst and wherein a weight ratio between the palladium and the silver in the catalyst is from about 0.1:1 to about 5:1.

4. The catalyst of claim 1, wherein a ratio between a geometric surface of the shaped body and a volume of the shaped body is from about 0.5:1 to about 20:1.

5. The catalyst of claim 1, wherein a ratio between a geometric surface area of the shaped body and a volume of the shaped body is from about 1.4:1 to about 4:1.

6. The catalyst of claim 1, wherein the palladium comprises from about 0.01 to about 1 weight percent of the catalyst.

7. The catalyst of claim 1 wherein the support comprises aluminum oxide.

8. The catalyst of claim 7 wherein the aluminum oxide comprises substantially theta aluminum oxide.

9. The catalyst of claim 1 wherein the BET surface area of the support is from about 10 to 300 m²/g.

10. The catalyst of claim 1 wherein the BET surface area of the support is from about 30 to 80 m²/g.

11. The catalyst of claim 1 wherein a diameter of the trilobal shaped body is from about 3 to 10 nm, a length is from about 3 to 15 nm and a diameter of an opening in a lobe of the trilobal shaped body is from about 0.5 to 5 nm.

12. The catalyst of claim 1 further comprises from about 0.01 to about 0.1 weight percent of a material selected from a group consisting of an alkali metal, an alkaline earth metal or mixtures thereof, wherein the weight percent is calculated in the form of oxides.

13. A method for production of the catalyst of claim 1 comprising preparing a shaped body having a trilobal cross-section in which lobes of the shaped body are provided with openings passing therethrough, impregnating the shaped body with a palladium salt solution, reducing the palladium salt solution to a palladium oxide with a reducing agent, washing, drying, and calcining the impregnated, shaped body and reducing the palladium oxide to a corresponding palladium metal.

14. The method of claim 13 comprising impregnating the shaped body with a silver salt and reducing the silver salt to silver metal.

15. The method of claim 13 wherein the reducing of the palladium salt is accomplished in an alkaline medium at a temperature from about 20 to about 100° C.

16. The method of claim 13 wherein the reducing of the palladium salt is accomplished in an aqueous alkaline solution.

17. A catalyst for hydrogenation of unsaturated hydrocarbons comprising catalytically active amounts of palladium on a support, wherein the support is a shaped body with a trilobal cross-section, wherein lobes of the trilobal shaped body are provided with openings passing therethrough and wherein the catalyst has a geometric surface from about 0.2 to 3 cm².

18. The catalyst of claim 17, having a geometric surface from about 0.7 to 1.2 cm².

19. The catalyst of claim 17, having a geometric surface from about 0.9 to 1.5 cm².

20. A catalyst for hydrogenation of unsaturated hydrocarbons comprising catalytically active amounts of palladium on a support, wherein the support is a shaped body with a trilobal cross-section, wherein lobes of the trilobal shaped body are provided with openings passing therethrough and wherein the catalyst further comprises palladium crystallites after catalyst reduction wherein at least about 80 percent of the palladium crystallites have a crystallite size from about 2 to 15 nm.

21. A catalyst for hydrogenation of unsaturated hydrocarbons comprising catalytically active amounts of palladium on a support, wherein the support is a shaped body with a trilobal cross-section, wherein lobes of the trilobal shaped body are provided with openings passing therethrough wherein a BET surface area of the support is from about 1 to 300 $m^2/g$ and wherein up to about 40 percent of the BET surface area is contained in pores with a diameter from about 1750 to 80 nm and at least about 60 percent of the BET surface area is contained in pores with a diameter from about 80 to 14 nm.

22. A catalyst for hydrogenation of unsaturated hydrocarbons comprising catalytically active amounts of palladium on a support, wherein the support is a shaped body with a trilobal cross-section, wherein lobes of the trilobal shaped body are provided with openings passing therethrough, and wherein the catalyst comprises palladium crystallites after catalyst reduction, wherein a ratio between a BET surface area of the catalyst and a size of the palladium crystallites is from about 0.1:1 to about 10:1.

* * * * *